US012453834B2

United States Patent

Dhuper

(10) Patent No.: US 12,453,834 B2
(45) Date of Patent: Oct. 28, 2025

(54) MODULAR PULMONARY TREATMENT SYSTEM

(71) Applicant: AEON RESEARCH AND TECHNOLOGY, INC., Hewlett, NY (US)

(72) Inventor: Sunil Kumar Dhuper, Old Westbury, NY (US)

(73) Assignee: AEON RESEARCH AND TECHNOLOGY, INC., Hewlett, NY (US)

(*) Notice: Subject to any disclaimer, the term of this patent is extended or adjusted under 35 U.S.C. 154(b) by 1000 days.

(21) Appl. No.: 17/307,579

(22) Filed: May 4, 2021

(65) Prior Publication Data

US 2021/0338964 A1 Nov. 4, 2021

Related U.S. Application Data

(60) Provisional application No. 63/149,748, filed on Feb. 16, 2021, provisional application No. 63/019,729, filed on May 4, 2020.

(51) Int. Cl.
*A61M 16/08* (2006.01)
*A61M 16/06* (2006.01)
(Continued)

(52) U.S. Cl.
CPC .... *A61M 16/0816* (2013.01); *A61M 16/0683* (2013.01); *A61M 16/105* (2013.01);
(Continued)

(58) Field of Classification Search
CPC .............. A61M 16/06; A61M 16/0683; A61M 16/0816; A61M 16/0833; A61M 16/0875;
(Continued)

(56) References Cited

U.S. PATENT DOCUMENTS 1,806,162 A * 5/1931 Hahn ........................ A43C 7/04 24/712.9
3,100,485 A * 8/1963 Bartlet, Jr. ............. A62B 9/003 137/154
(Continued)

FOREIGN PATENT DOCUMENTS

CN 110215590 A 9/2019
ES 1253693 U 10/2020
(Continued)

OTHER PUBLICATIONS

International Search Report and Written Opinion in PCT Application No. PCT/US22/11546, mailed May 16, 2022.
(Continued)

*Primary Examiner* — Brandy S Lee
*Assistant Examiner* — Mishal Zahra Hussain
(74) *Attorney, Agent, or Firm* — Leason Ellis LLP

(57) ABSTRACT

A protective headgear includes a main body (e.g., face mask) that is worn over the face. The main body has an inhalation port that is for fluid coupling to an inhalation gas source and at least one exhalation port. The headgear includes an HME unit that has an inhalation leg that is in fluid communication with the inhalation port and a top leg that is in fluid communication with the inhalation leg and the at least one exhalation port. The top leg has an open window formed therein. The HME unit further includes an HME membrane that is disposed within the top leg adjacent the open window such that the HME membrane completely covers the open window.

16 Claims, 13 Drawing Sheets

(51) Int. Cl.

| | |
|---|---|
| ***A61M 16/10*** | (2006.01) |
| ***A62B 18/02*** | (2006.01) |
| ***A62B 18/08*** | (2006.01) |
| ***A62B 23/02*** | (2006.01) |

(52) U.S. Cl.
CPC ............ *A62B 18/02* (2013.01); *A62B 18/084* (2013.01); *A62B 23/02* (2013.01); *A61M 2205/126* (2013.01)

(58) Field of Classification Search
CPC .............. A61M 16/1045; A61M 16/20; A61M 2205/126; A61M 16/105; A61M 16/1055; A61M 16/106; A61M 16/1065; A61M 16/107; A61M 16/0093; A62B 18/02; A62B 18/025; A62B 18/04; A62B 18/045; A62B 18/06; A62B 18/084; A62B 23/02; A62B 7/10; A62B 9/003
See application file for complete search history.

(56) References Cited

U.S. PATENT DOCUMENTS 6,478,026 B1 * 11/2002 Wood ................ A61M 16/1055 128/207.18
9,320,923 B2 * 4/2016 Koehler ............. A41D 13/1146
9,427,545 B2 * 8/2016 Eves ................. A61M 16/0655
D952,322 S * 5/2022 Chang ............................ D2/978
2013/0186394 A1 * 7/2013 Hallett .............. A61M 16/0057 128/205.24
2016/0029745 A1 * 2/2016 Atherinos ................ A43C 7/00 24/712.1
2016/0158475 A1 * 6/2016 Harrison ............. A61M 16/105 128/205.12
2017/0100558 A1 * 4/2017 Dhuper ............. A61M 16/0875
2018/0200467 A1 7/2018 Finch
2020/0001028 A1 * 1/2020 Mehta ............... A61M 16/1045
2020/0268995 A1 8/2020 Shin
2020/0282174 A1 9/2020 Dhuper et al.
2020/0360641 A1 11/2020 Dhuper et al.

FOREIGN PATENT DOCUMENTS

IT UB20154629 A1 4/2017
WO WO-2020113349 A1 * 6/2020

OTHER PUBLICATIONS

Supplemental European Search Report in EP Application No. 22756666.8-1122/4294535, mailed Jan. 7, 2025 (10 pages).

* cited by examiner

MODULAR PULMONARY TREATMENT SYSTEM

CROSS-REFERENCE TO RELATED APPLICATION

The present applications claims priority to and the benefit of U.S. patent application Ser. No. 63/019,729, filed May 4, 2020, and U.S. patent application Ser. No. 63/149,748, filed Feb. 16, 2021, each of which is hereby expressly incorporated by reference in its entirety.

TECHNICAL FIELD

The present invention relates to pulmonary treatment equipment and more particularly, relates to a patient interface, such as a mask, that is configured to operate in a number of different modes including but not limited to delivery of a gas (e.g., oxygen or an oxygen mix) to a patient; delivery of an aerosolized medication (drug) to a patient; and a combination thereof. The modular pulmonary treatment device includes one or more exhalation ports with are fitted with a particulate filter, such as an N95 filter, that is effective at filtering particulates, such as influenza and COVID-19 virus, etc. The modular pulmonary treatment device also includes an HME (heat moisture exchange) that is disposed within both the inhalation path and the exhalation path.

BACKGROUND

In the battle against respiratory diseases, such as influenza and COVID-19, it is often necessary to provide oxygen to the patient using different means including the use of a face mask that is fluidly connected to a gas source (oxygen source). It is necessary that the face mask be sealed to the face to effectively deliver the oxygen and also because these respiratory diseases are transmitted on droplets of excretions from sneezing and coughing, it is important to protect others, including the healthcare providers, from these droplets that are expelled from the patient.

Coronavirus COVID-19 is a highly transmissible. While it endangers the human species, health care work force that is caring for the infected patients and are in close contact with the patients are at a much greater risk of acquiring the infection. The risk continues to increase from outpatient ambulatory care/urgent care centers to EMS first responders, ED staff, Inpatient clinical and support staff. Most patients evaluated by the first responders, many who come to the ED, and most who are in the inpatient clinics require oxygen therapy due to hypoxia. Oxygen requirement may vary from 21% to 100% during spontaneous breathing. Some patients may require oxygen delivery via high flow nasal cannula and non-invasive positive pressure ventilation. Some very sick patients may require mechanical ventilation with high FiO2 and high levels of PEEP.

Oxygen delivery in spontaneously breathing patients poses an astronomical risk of virus transmission to those caring for the patient. Any flow, low or high via nasal cannula or facemask, or NIPPV aerosolizes the virus particles from the oronasal passages, remains suspended in the air, and can be inhaled by the healthcare workforce caring for the patient. All oxygen delivery systems are fraught with the problem of leakage of the aerosolized virus particles. It is understood that regular nasal cannulas are a wide open system, and so are high flow nasal cannula. Even partially closed systems like the face masks have significant leakage around the borders of the mask. In addition, the exhaled virus particles freely flow out of the mask through the exhalation ports in the mask. When using NIPPV, the problem is accentuated manifold due to the positive pressure. The exhaled particles and the plumes generated can travel a significant distance even in a confined space and pose significant risk to the care takers of the patients. No mask used by the healthcare workforce is 100% protective and hence the risk of transmission of this deadly virus remains.

Every measure that could be adopted to mitigate the spread of aerosolized virus particles can save lives. It is our intent through this new invention to mitigate the spread of virus to the healthcare workforce caring for the patients.

The combination of a separate eye shield, typically attached to a head band, is also not desirable since there is a large dead space of air between the shield and the underlying mask. This dead air space can collect CO2 and also can trap and collection undesirable virus particles, etc.

SUMMARY

A protective headgear includes a main body (e.g., face mask) that is worn over the face. The main body has an inhalation port that is for fluid coupling to an inhalation gas source and at least one exhalation port. The headgear includes an HME unit that has an inhalation leg that is in fluid communication with the inhalation port and a top leg that is in fluid communication with the inhalation leg and at least one exhalation port. The top leg has an open window formed therein. The HME unit further includes an HME membrane that is disposed within the top leg adjacent the open window such that the HME membrane completely covers the open window.

BRIEF DESCRIPTION OF DRAWING FIGURES

DETAILED DESCRIPTION OF CERTAIN EMBODIMENTS

Figure 1:
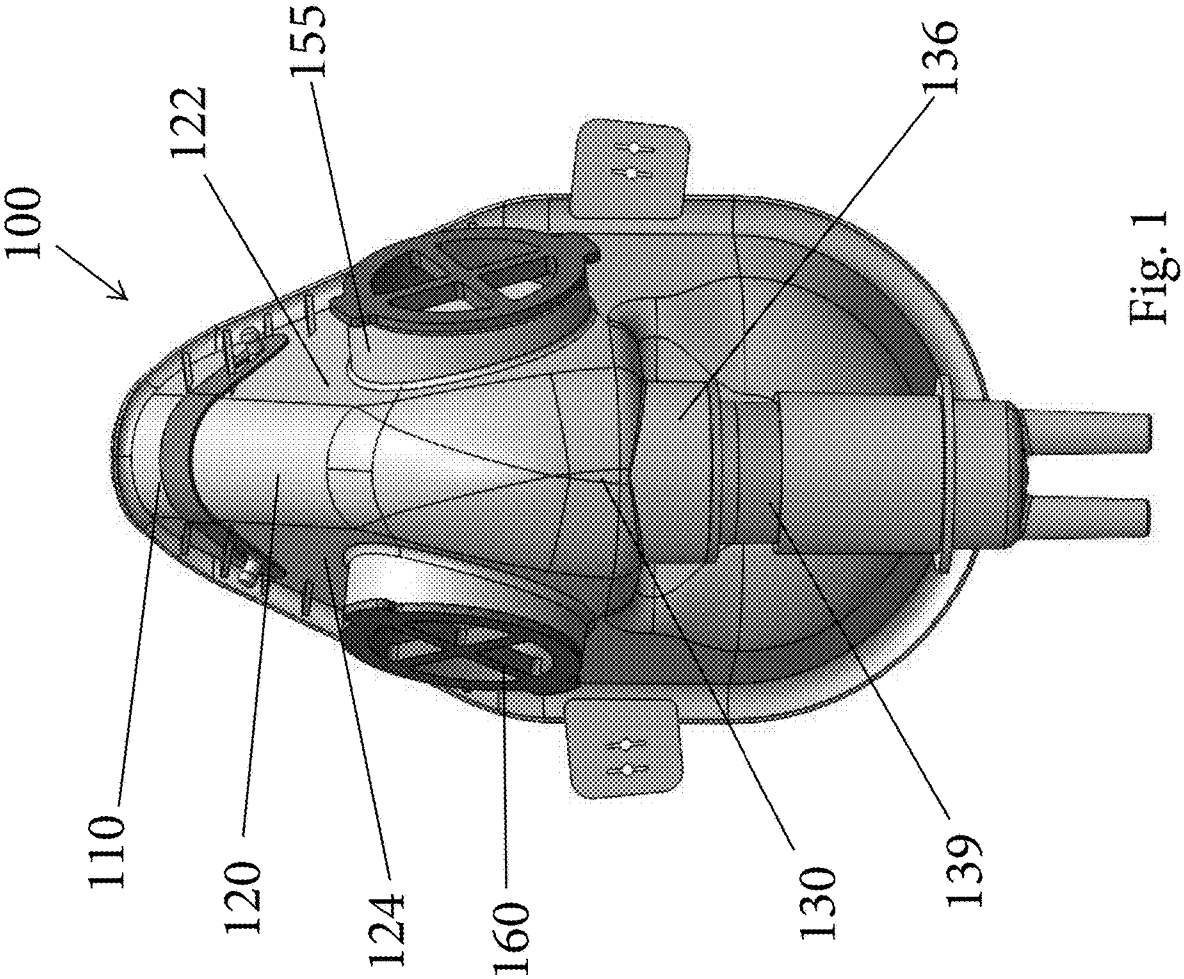
FIG. 1 is a front elevation view of a patient interface with an internal HME unit.

FIGS. 1-10 illustrate a patient interface 100, according to one embodiment, that is typically in the form of a face mask that is intended to be worn over the patient's face with both the nose and mouth being located inside the face mask. The patient interface 100 has a main body 110 that has a center nose portion 120 that includes a forward section 130, a first side 122 and an opposite second side 124 with a center nose bridge section 126 being located between the first side 122 and the second side 124. The forward section 130 includes a bottom face (underside) 132. The bottom face 132 can have a defined inhalation port 136 to which a gas supply conduit 139 can be attached. In the illustrated embodiment, the defined port 136 can be in the form of a tubular structure and the gas supply conduit can be a gas line (conduit) that is in fluid communication with a gas source, such as an oxygen source. In the illustrated embodiment, a flow connector 10 and a venturi 20 can be connected in series for delivering gas into the interior of the patient interface 100 and to the patient. Typically, the gas source is an oxygen source; however, other gas sources can be used including an oxygen mixture. A friction fit can be established between these parts.

Figure 6:
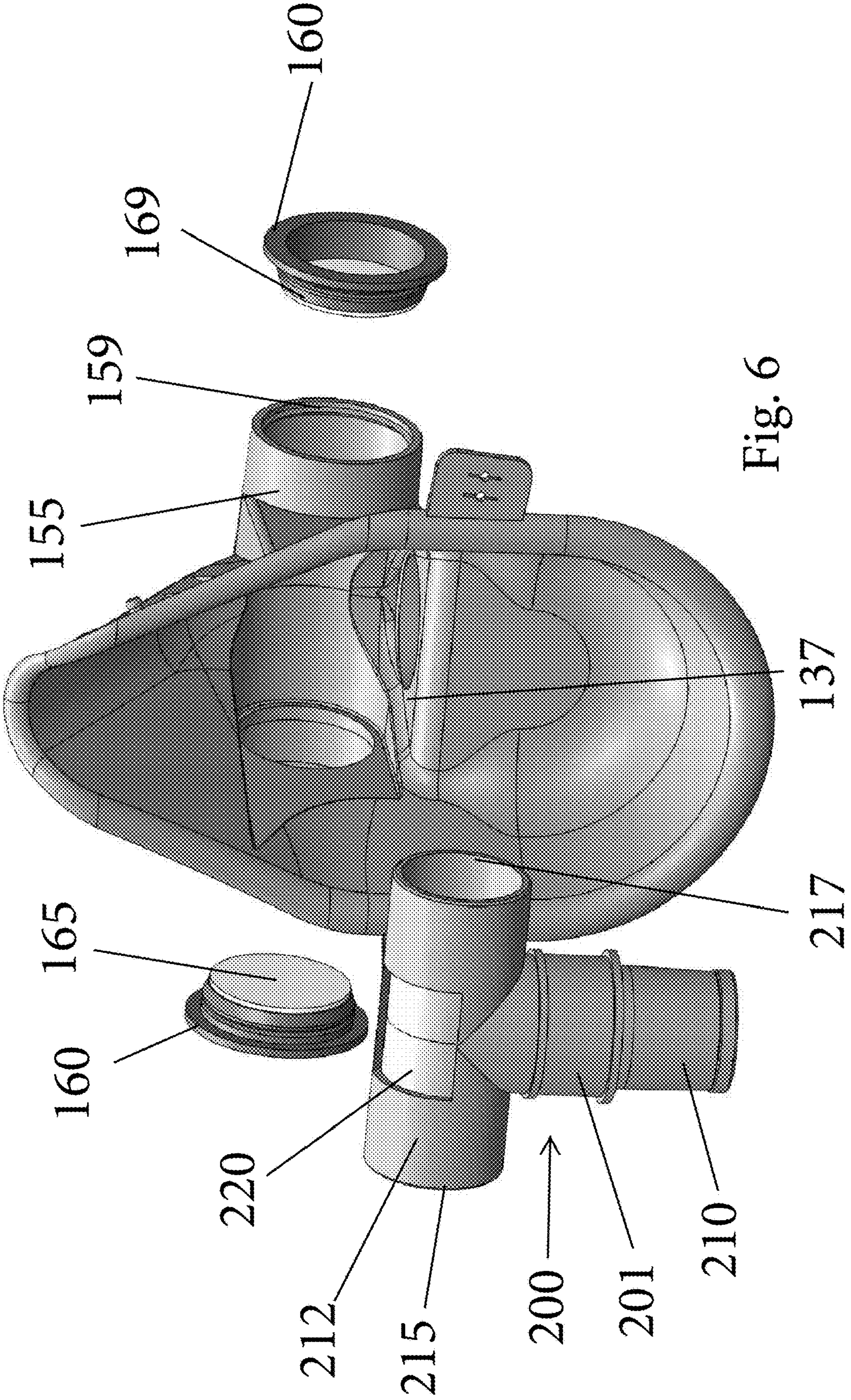
FIG. 6 is an exploded rear perspective view.

As shown in FIG. 6, the defined port 136 has a top opening that is formed along an inner shelf 137.

The inhalation port 136 is thus configured to receive a gas for delivery inside the mask body 110 to the patient. The inhalation port 136 can be an open connector or alternatively, the port 136 can be provided with and can be in communication with at least one inhalation valve to allow inflow of breathing gas to the patient. As described below, the inhalation port 136 is fluidly connected to a gas source (not shown) such as by a tube or the like. As described below, any number of other accessories can be attached to the inhalation port 136 to control the inflow of gas such as a venturi device, nebulizer, a single or dual reservoirs, etc. Many of these accessories allow the level of oxygen to be metered.

It will be appreciated that in one embodiment there is no inhalation valve but instead, the inhalation port 136 is a port that allows for an accessory to be attached to deliver oxygen. For example, tubing or other accessories can be sealingly attached to the port 136. In other embodiments, an inhalation valve can be provided.

Alternatively, an inhalation filter cartridge can be attached to the inhalation port 136. The cartridge can include a cartridge body that holds a filter such as the type described herein. The air entering the mask body 110 is thus filtered as the wearer inhales. This operating mode can be used when the wearer is outdoors entering a store, in high density spaces, etc. The inhalation cartridge is easily detached from the port 136 allowing the system to convert into a system in which oxygen is delivered via tubing to the port 136.

The modular pulmonary treatment device 100 can thus be any number of mask based devices that allow for the controlled delivery of a gas (oxygen) to the patient and of course, allowing the patient to freely exhale.

More details concerning suitable mask bodies 110 are disclosed in commonly assigned US patent application publication No. 2016/0158477 and U.S. Pat. No. 9,498,592, each of which is hereby expressly incorporated by reference in its entirety. These documents describe and illustrate a great number of face masks that can comprise the device 100 and also describe operating modes and accessories that can be used with the modular pulmonary treatment device 100. For example, a venturi device can be attached to the inhalation port 136 to allow for controlled delivery of oxygen at a selected concentration, such as between 21% and 100% of the total gas delivered to the patient. Thus, a high flow delivery venturi can be used. A nebulizer and/or reservoir collection bag can be used as disclosed in Applicant's own prior work, such as those incorporated by reference documents mentioned herein.

Exhalation Port with Particulate Filter

Respirator masks and filters are commonly identified by a respirator rating letter class and respirator rating numbering class. For example, the respirator rating letter class is one of the following: N—not oil resistant, R— resistant to oil, and P—oil proof. Respirator rating number class is one of the following: 95—Removes 95% of all particles that are at least 0.3 microns in diameter, 99—Removes 99% of particles that are at least 0.3 microns in diameter, and 100—Removes 99.97% of all particles that are 0.3 microns in diameter or larger.

As is known, harmful viruses, such as the flu virus and COVID-19 virus, can be 0.17 microns in size which is smaller than even N100 filters can filter out. These viruses are typically transported from patient to patient on droplets of excretions from sneezing and coughing; however, it may be possible for the virus particles themselves to be suspended in air. These particles are typically 5 microns or larger. When a sick patient wears a respirator, the respirator can be very effective at preventing infectious material from leaving the patient's body and exposing others, including healthcare workers, to the virus, and when worn by healthy individuals, it prevents inhalation of said material.

The mask body 110 can also include at least one exhalation port 150 can include an exhalation filter assembly that can consist of a detachable filter body 160 that holds a filter 165. Alternatively, the exhalation port 150 can include an exhalation valve assembly that includes the filter 165 for filtering the exhaled gas. The filter 165 is positioned such that the exhaled air must pass through the filter 165 before existing the mask body 110 into the atmosphere. The filter 165 is thus preferably configured to filter out virus particles and other pathogens, etc. For example, the filter 165 can be an N95, N99 or N100 filter.

As shown, the mask body 110 can include two exhalation ports 150 on the opposite sides 122, 124. The exhalation port 150 comprises a hole formed in the mask body 110 and can include a perimeter wall 155 that protrudes outwardly from the mask body 110 and as shown in FIG. 6 and other figures, the perimeter wall 155 can include inner threads 159. In the illustrated embodiment, the perimeter wall 155 is in the form of an annular shaped wall. As shown in FIG. 6, a first axis that passes through the ports 150 and a second axis passing through the defined port 136 is perpendicular to the first axis.

The detachable filter body 160 is shaped and sized to mate with the perimeter wall 155 for sealingly attaching the filter cartridge to the mask body 110. To mate with the port 150, the filter body 160 can include exterior threads 169 that mate with the inner threads 159. For example, the filter body 160 is screwed onto the perimeter wall 155. Alternatively, the filter body 160 can be in the form of a plastic body that frictionally mates with the perimeter wall 115 and is frictionally held therein. The filter body 160 itself includes one or more holes that are covered by the filter 165. In one illustrated embodiment, the exhalation port 150 includes an inner frame 151 (e.g., a cross shaped rib structure) that defines a plurality of holes and similarly, inside the filter body 160 there is an inner frame 161 (e.g., a cross shaped rib structure) that defines a plurality of holes. The numbers of holes in the port 150 and the filter body 160 can be different. The inner frame 151 also serves to limit the inward travel of the filter body 160 and provides a surface against which the filter body can rest when inserted into the port 150.

Figure 2:
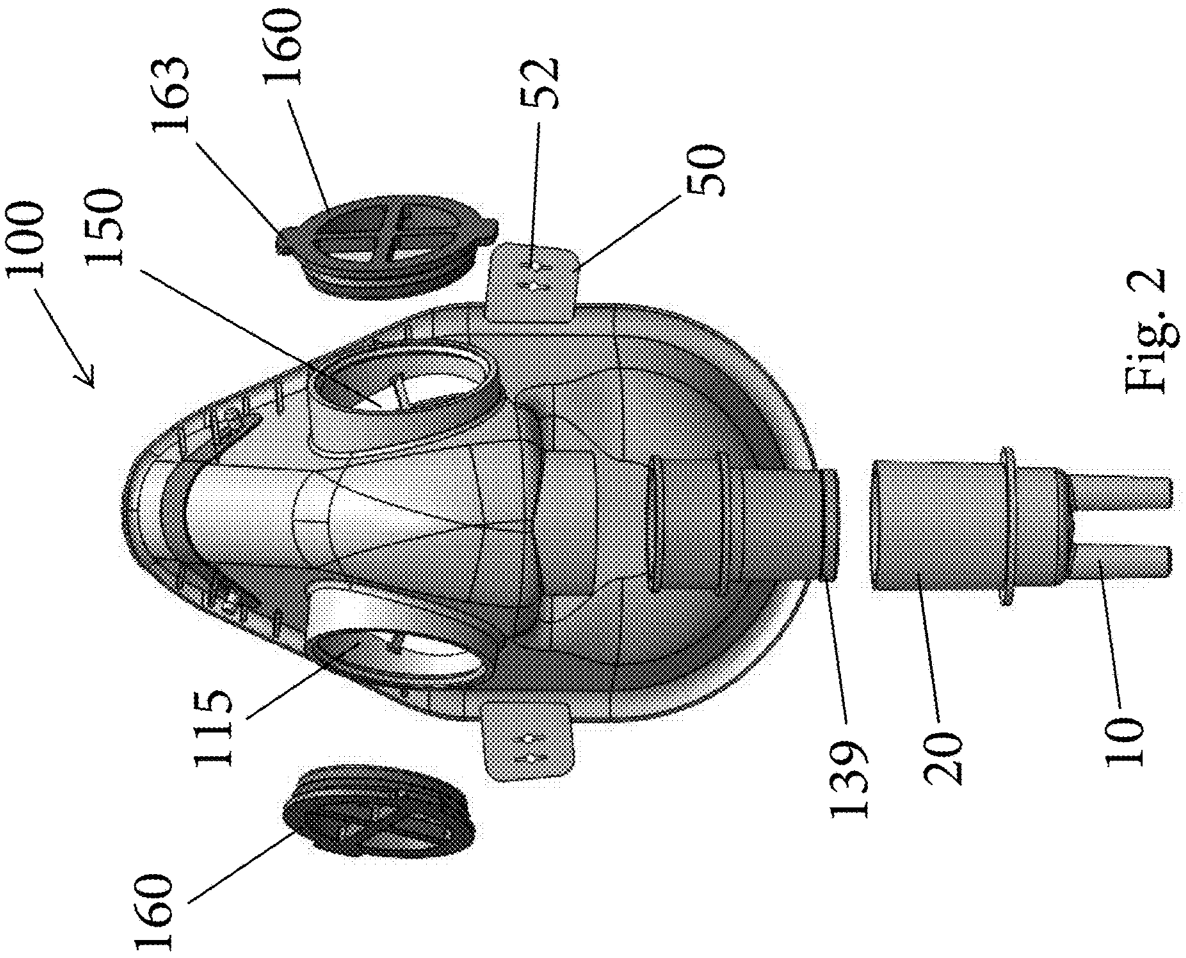
FIG. 2 is an exploded perspective view thereof.
Figure 3:
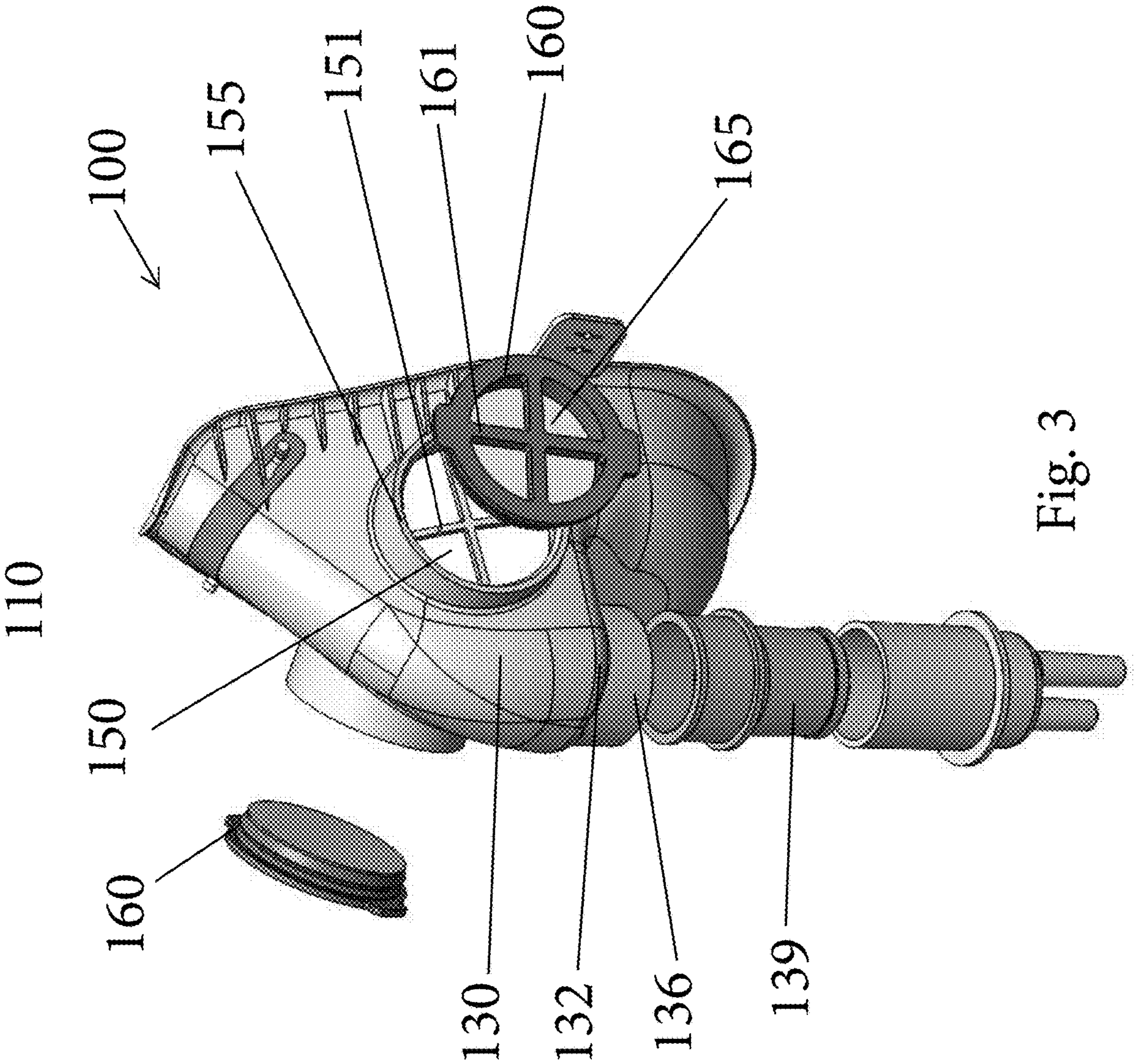
FIG. 3 is an exploded side perspective view thereof.
Figure 4:
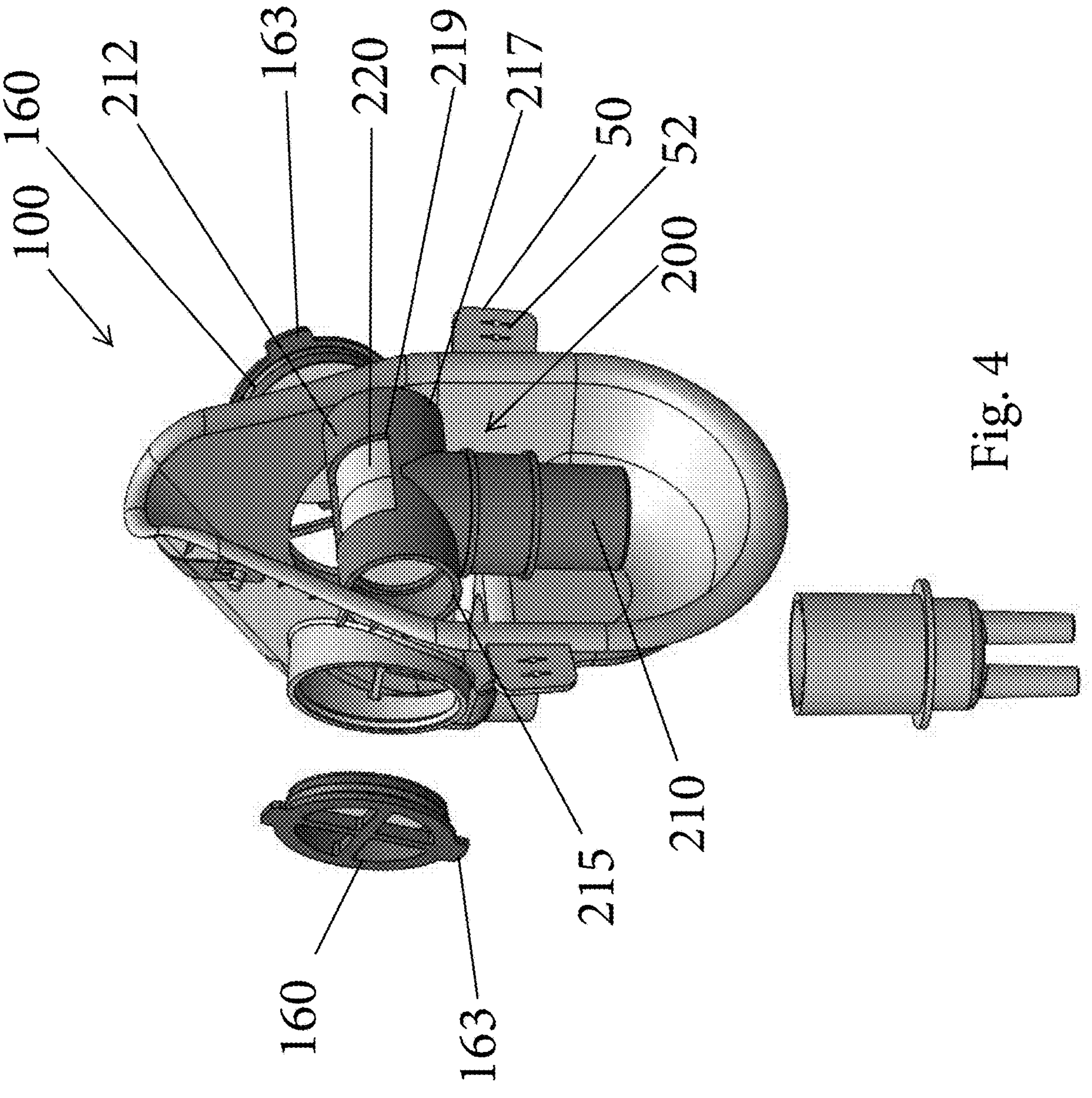
FIG. 4 is an exploded rear perspective view.
Figure 5:
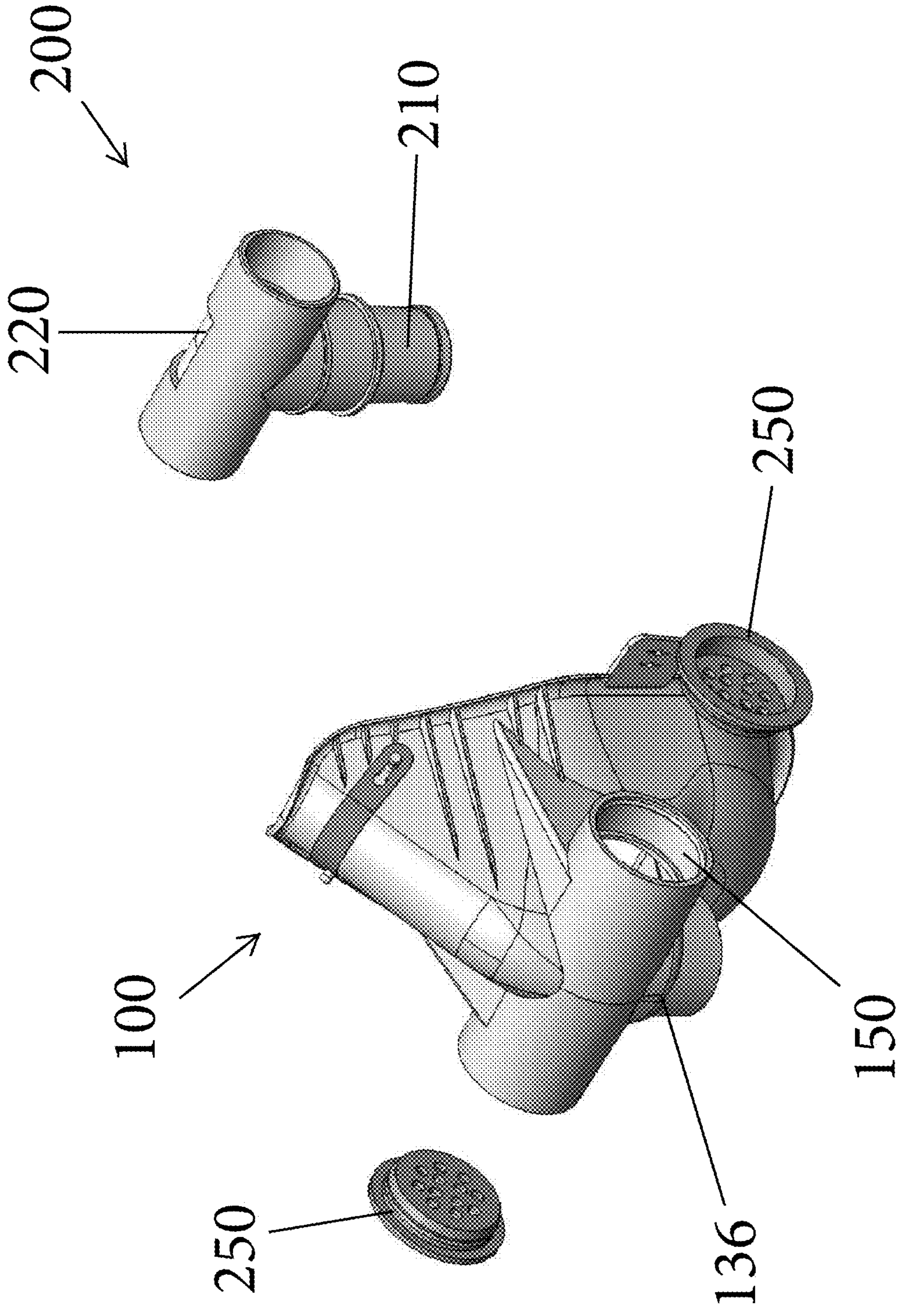
FIG. 5 is an exploded front perspective view.

As shown in FIG. 2, one filter body 160 can include side tabs 163 that permit the filter body 160 to be more easily held and more easily inserted and removed from the exhalation port 150. The detachable exhalation filter cartridges can be fit to the ports 150 using any number of traditional techniques, such as a friction fit or they can be screwed into the ports 150 in which case the detachable exhalation filter cartridge and the respective port 150 includes threads.

As described herein, in one operating mode, the detachable exhalation filter cartridges are removed from the mask body 110 resulting in the exhalation ports 150 being completely open. In this mode, the exhaled air exits through these open ports 150 and does not pass through filters 165. In the alternative embodiment, when the detachable exhalation filter cartridges are inserted into the ports 150, the exhaled air passes through the filters 165 before exiting the mask body 110.

Figure 7:
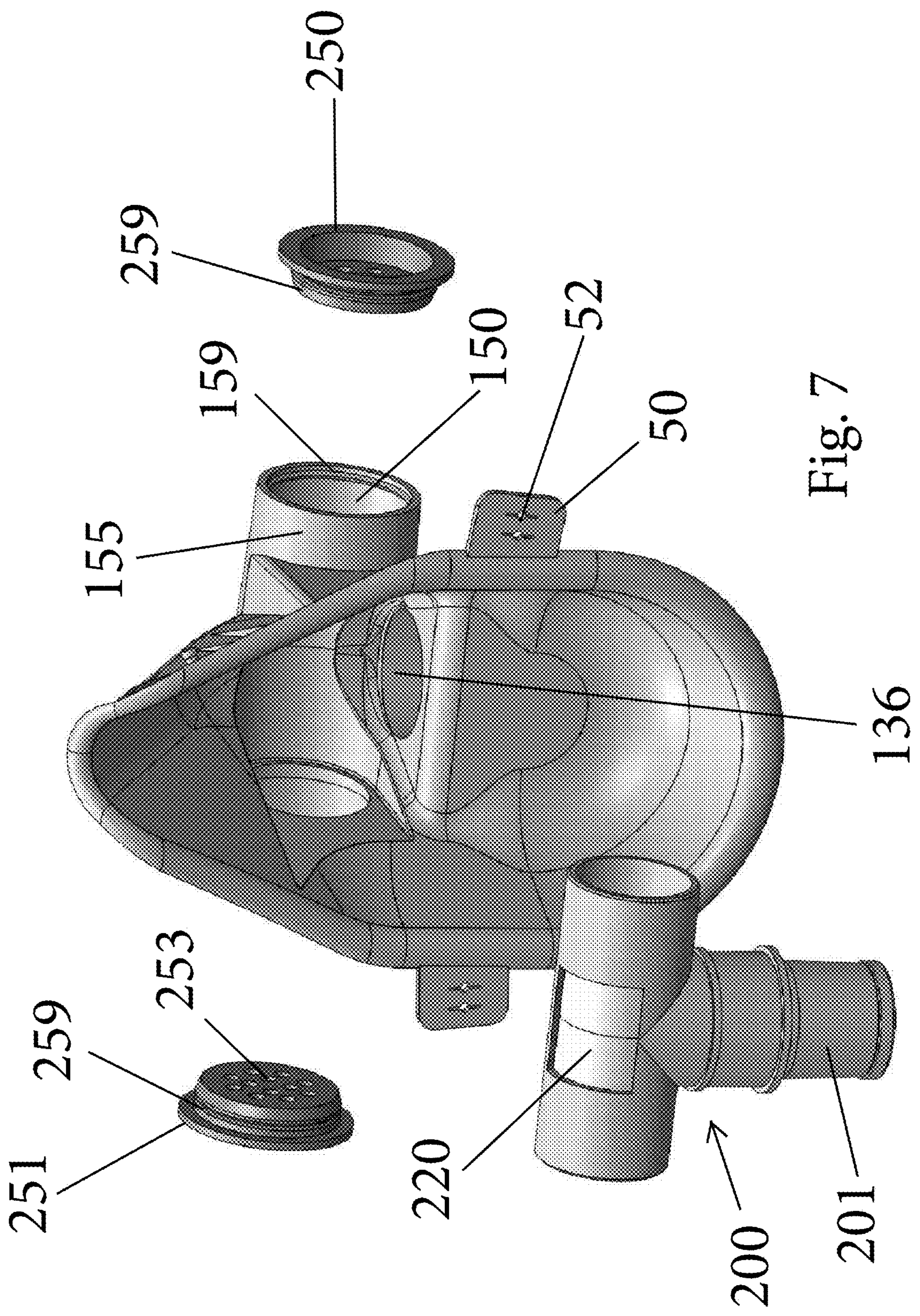
FIG. 7 is another exploded rear perspective view.

FIG. 7 shows alternative detachable filter bodies 250 that are configured to mate with the port 150. The filter body 250 can include exterior threads 259 that mate with the inner threads 159. For example, the filter body 250 is screwed onto the perimeter wall 155.

In yet another embodiment, the detachable filter bodies 160, 250 can be eliminated and the ends of the HME unit 200 remain open.

HME Unit

The device 100 also includes an HME unit 200. As is known, the basic components of heat and moisture exchangers (HMEs) 200 are foam, paper, or a substance which acts as a condensation and absorption surface. The material is often impregnated with hygroscopic salts such as calcium chloride, to enhance the water-retaining capacity. HMEs used for laryngectomees are mostly hygroscopic.

In accordance with the present invention, the HME unit 200 is located within both the inhalation flow path and the exhalation flow path of the device 100. In other words, inhaled gas must flow through the HME unit 200 and exhaled gas must flow through the HME unit 200 before exiting the mask body 110.

The HME unit 200 comprises an HME canister or body 201 and includes one or more HME membranes 220. As illustrated, the HME body can be in the shape of a T that includes a bottom leg 210 that intersects a top horizontal leg 212 at a right angle. The top horizontal leg 212 is open at a first end 215 and an opposite second end 217. The bottom leg 210 is open along its bottom as well. The legs 210, 212 can have different dimensions (e.g., different lengths). In the illustrated embodiment, the legs 210, 212 can have tubular shapes.

While a T-shape (90 degree offset) is one preferred construction for the HME body, it will be appreciated that other shapes are possible in that the angle between the bottom leg 210 and the top horizontal leg 212 is not limited to being 90 degrees but instead can be other angles.

The ends 215, 217 of the top horizontal leg 212 are configured to sealingly mate with the exhalation ports 150 when the HME unit 200 is inserted into and coupled to the interior of the mask body 110.

In one aspect of the present disclosure, the top horizontal leg 212 includes a window 219 that is open to the interior of the mask body 110. The window 219 can take any number of different shapes and sizes. In the illustrated embodiment, the window 219 has a rectangular shape that is formed in the side wall of the tubular shaped top horizontal leg 212. The window 219 faces upward within the interior of the mask body 110.

The bottom leg 210 can be disposed through a hole formed in the bottom of the mask body 110 and be provided for attachment to a connector. Alternatively, the bottom of the mask body 110 includes a connector or adapter to which the bottom leg 210 attaches. The bottom leg 210 is thus placed in fluid communication with the defined inhalation port 136 and the gas supply conduit 139 to allow the oxygen (or mixed oxygen) to be delivered from the external gas source to the interior of the mask body 110.

In the illustrated embodiment, there are one or more HME membranes 220 that are in the form of one or more disks that are positioned inside the top horizontal leg 212. The HME membranes 220 are sealed against the inner wall of the top horizontal leg 212. The HME membranes 220 are positioned such that they are adjacent to the entire area of the window 219. While the illustrated embodiment shows two side-by-side HME membranes 220, it will be appreciated that instead there can be a single HME membrane 220 having the same or similar dimensions as two side-by-side HME membranes 220.

This orientation of the two HME membranes 220 serves two purposes. The first is that the inhalation gas that flows through the bottom leg 210 and then through the HME membranes 220 and exits through the window 219 to the patient. The second is that the exhalation gases must flow through the HME membranes 220 to exit through the exhalation ports 150 to atmosphere. More specifically, exhalation gases flow through the window 219 through the HME membranes 229 to the exhalation ports 150.

The HME unit 200 is thus purposely formed and positioned such that both inhaled and exhaled air pass through the HME membranes 220. Due to the sealed connection of the ends 215, 217 to the exhalation ports 150 and the sealed connection of the bottom leg 210 to a conduit structure that carries the inhalation gas, the HME unit 200 is in a sealed, leak proof environment and both inhalation and exhalation gases must flow through the HME unit 200.

As described in the '477 publication, in a different embodiment, an exhalation valve and filter can be part of a detachable cartridge that is detachable from the mask body 110 to allow for replacement of the filter 165. In one embodiment, the exhalation valve assembly has a valve seat to which the exhalation valve seats and then the filter 165 is upstream of the valve so that exhaled air passes through the filter and then passes the open valve. Alternatively, the filter 165 can be located downstream of the valve so that exhaled air passing by the open valve then contacts and passes through the filter.

When there is no exhalation valve, only the filter is provided in the cartridge body that is detachably attached to the port 150 to filter the exhaled air.

In the illustrated mask body 110, there are two exhalation ports 150; however, there can only be a single larger port or more than two ports. For each exhalation port 150 there is a corresponding detachable filter body 160 (e.g., exhalation cartridge).

It will be appreciated that the protective headgear (device) 100 is closed system in that the caregivers are protected from the wearer, while the device 100 is configured to allow for flow of oxygen or other gas or a mixture to the patient to treat a respiratory condition.

Figure 8:
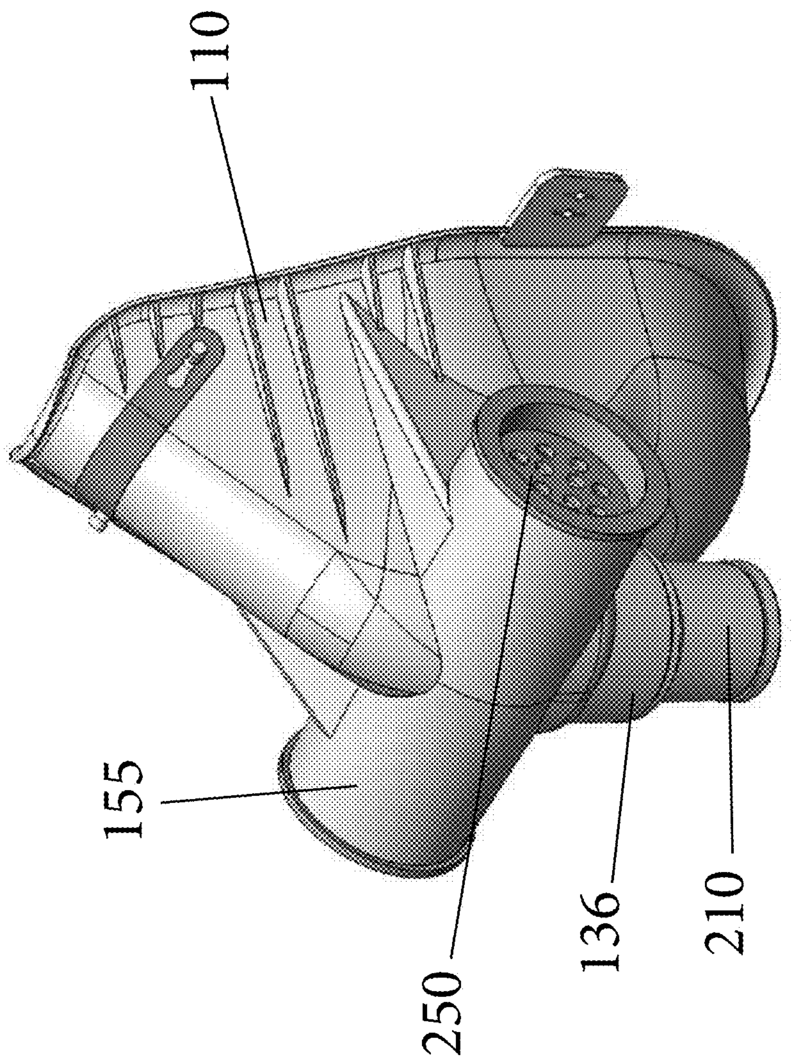
FIG. 8 is a front perspective view.
Figure 9:
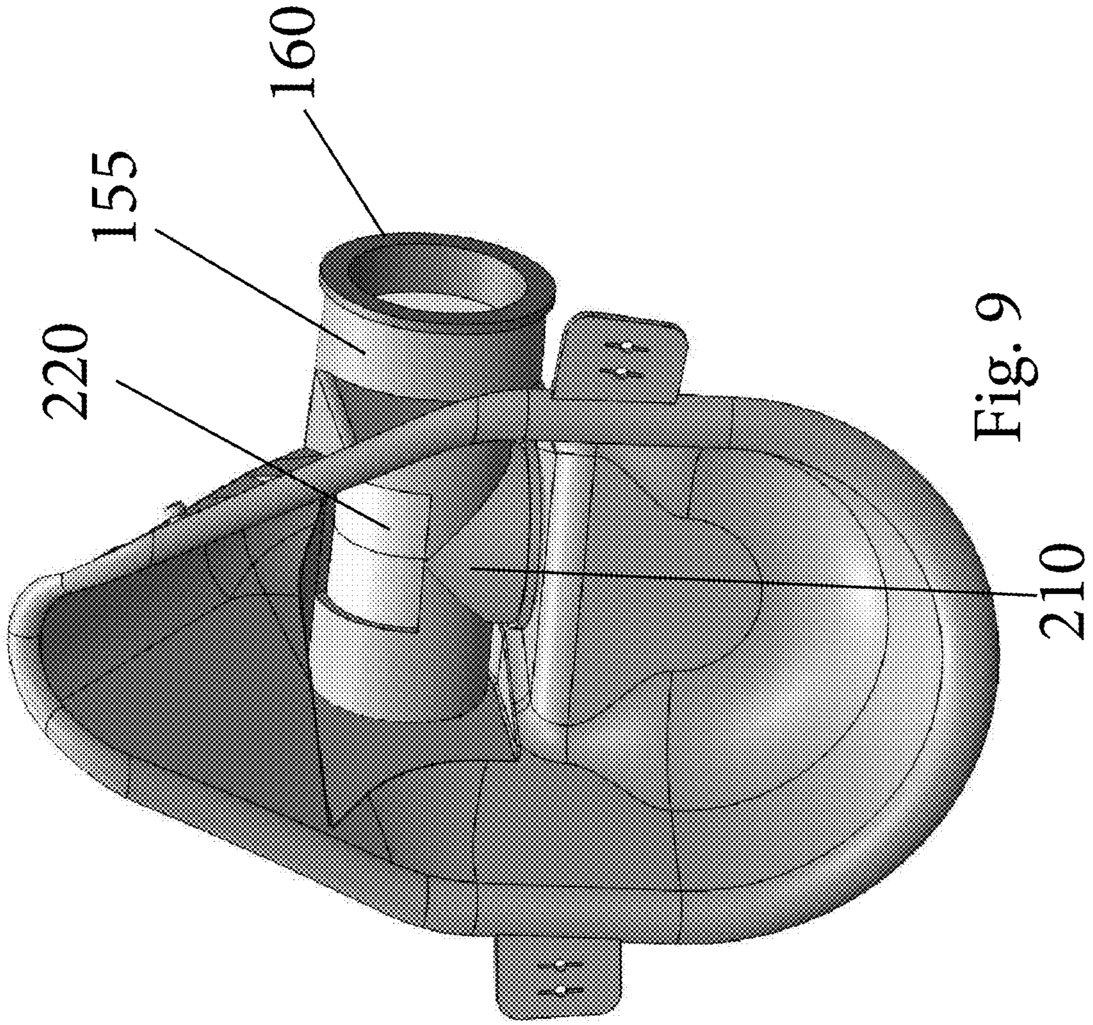
FIG. 9 is a rear perspective view.
Figure 10:
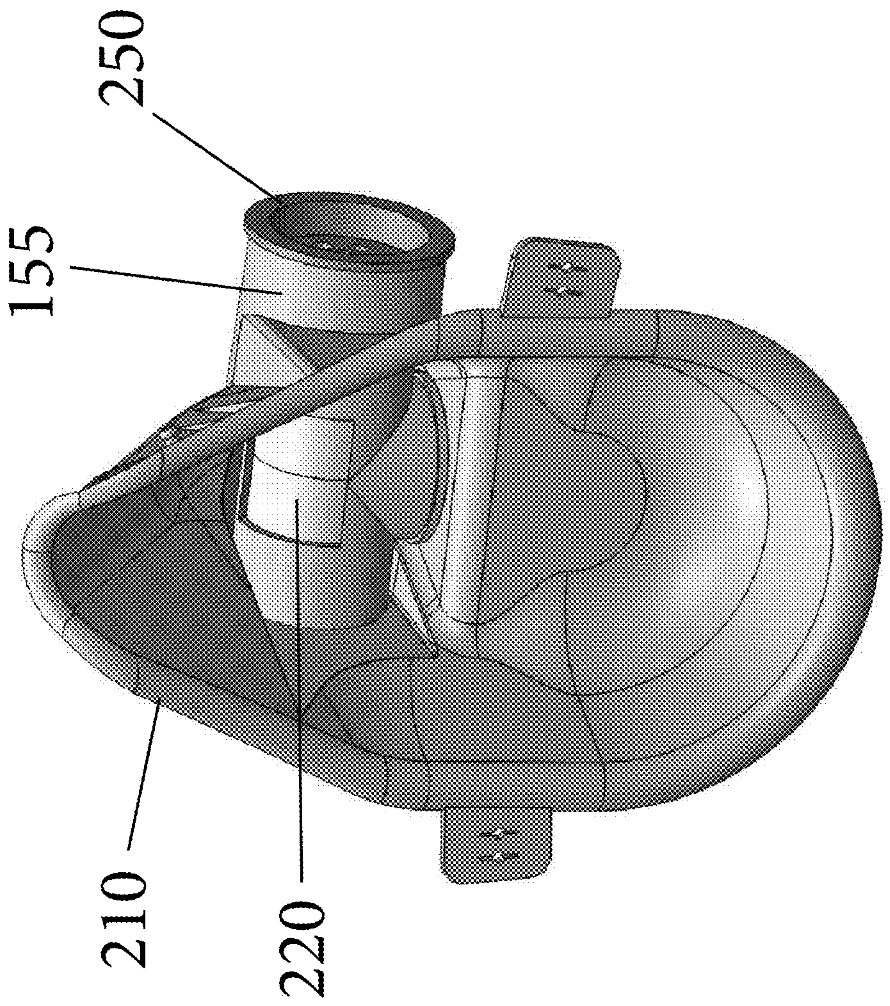
FIG. 10 is another rear perspective view.

FIGS. 8-10 illustrate the HME unit 200 in the installed position. In this installed position, the ends of the HME unit 200 are sealed relative to the ports 150 and therefore exhaled air can only exit the headgear 100 by flowing through the HME unit 200 to the ports 150. In other words, the HME unit 200 is located along the exhalation path. Similarly, the HME unit 200 is located along the inhalation path since the inhalation gas must flow into the HME unit 200 before being inhaled by the patient. This results by sealingly coupling the HME unit 200 to both the exhalation ports and the inhalation port.

The patient interface (mask) can have a pair of side strap attachment tabs 50 that are provided on either side of the face mask. Each tab 50 has one or more slits 52 for receiving a strap (not shown) that is designed to be fitted about the wearer's head. In accordance with the present application, each slit 52 has a round center opening and two linear end sections. The present applicant has discovered that the inclusion of the round center opening in the slit makes is easier to insert the end of the strap and then subsequently attach the strap to the tab 50.

One important aspect of the present device is that all of the inhaled air that enters into the patient interface (mask) passes through the HME unit 200 and similarly, all of the exhaled air from the patient passes through the HME unit 200. In this way, the system is a closed, sealed system in which 100% of both inhaled air and exhaled gases pass through the IME unit 200.

Figure 11:
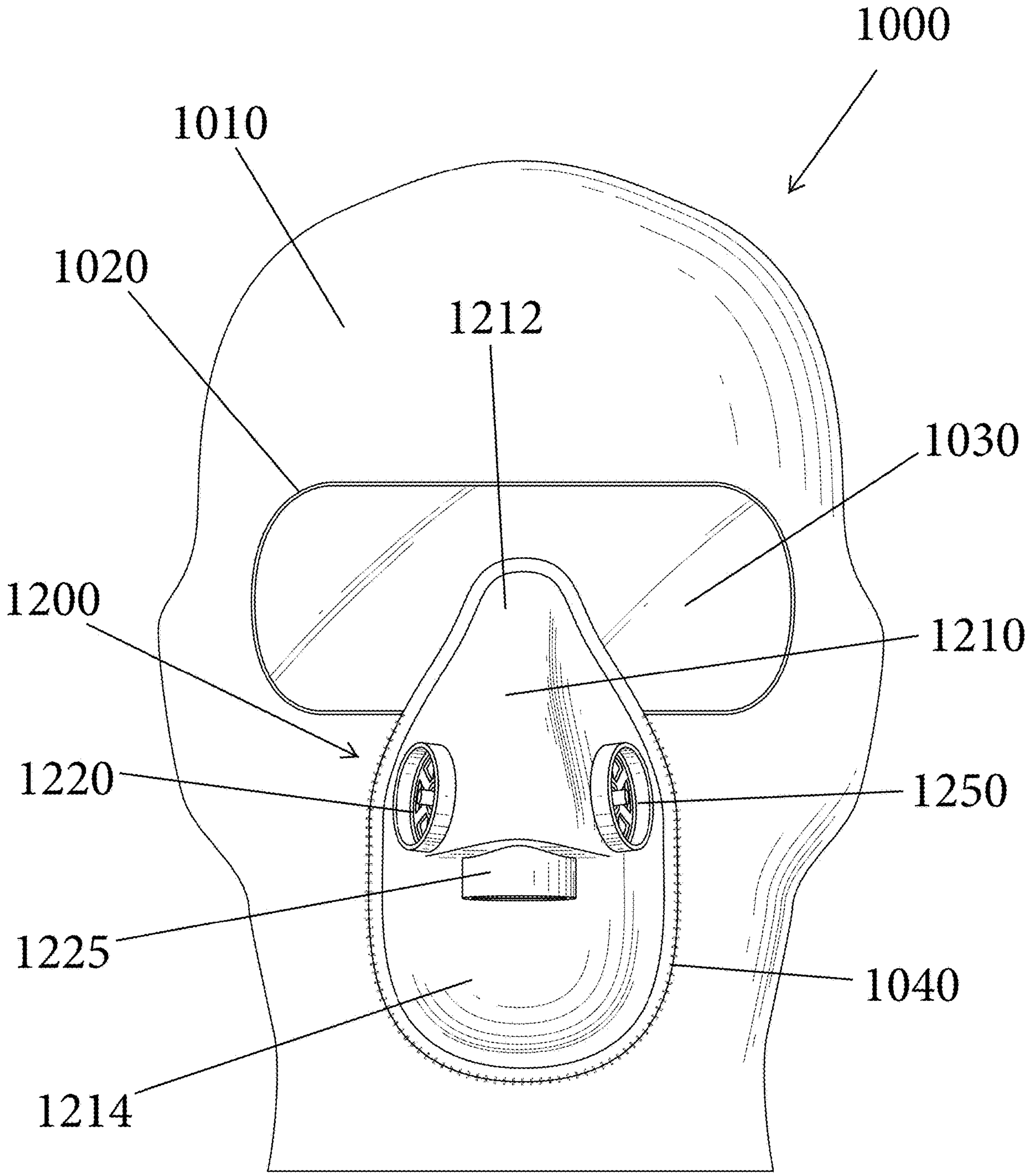
FIG. 11 is a front elevation view of another patient interface.

FIG. 11 illustrates another complete headgear 1000 with integral modular pulmonary treatment device 1200 incorporated therein. As described herein, the complete headgear 1000 is designed to be worn over the head of the user such that it covers the back and top of the head as well as the face of the user and extends around the neck of the user. In this sense, the complete headgear 1000 resembles a ski mask. As is known, a ski mask is a form of protective covering that is designed to expose only part of the face, usually the eyes and mouth.

The complete headgear 1000 is defined by a main body 1100 that is formed of a suitable material, such as a fabric and can take any number of forms including woven or non-woven structures.

The main body 1100 of the headgear is typically underside and is stretched in order to place over the head of the wearer. Thus, a tight fit is achieved since the main body 1100 has elasticity and is tight against the head.

Unlike a traditional ski mask, the complete headgear 1000 is designed to be used in high risk contagious areas, such as a hospital and therefore, additional features are incorporated into the complete headgear to allow for such use.

First, the main body 1100 includes an eye (first) opening 1200 that is for placement over the eyes of the user. However, given the intended use of the complete headgear 1000, the eye opening 1200 is closed off by a transparent protective eye covering 1300, such as a flexible transparent plastic film that is attached to the main body 1100 within the eye opening 1200. This protective eye covering 1300 thus is placed over the eyes and provides an anti-microbial barrier that prevents virus particles from the entering the eyes. Any number of suitable flexible, clear transparent plastic films are commercially available.

Any number of techniques can be used to attach the protective eye covering 1300 to the main body 1100. For example, an adhesive can be applied along the peripheral edge of the protective eye covering 1300 for securing the eye covering 1300 to the main body 1100. Alternatively, the eye covering 1300 can be stitched to the main body 1100. Any number of other techniques can be used to sealingly attach the eye covering 1300 to the main body 1100.

In addition, the main body 1100 includes a nose and mouth (second) opening 1400 that is located such that when the headgear 1000 is worn, this opening 1400 is placed over the nose and mouth of the user. Instead of being completely open to atmosphere, the modular pulmonary treatment device 1200 is disposed within the opening 1400 and, as described herein, not only provides a protective structure that covers the nose and mouth but also is configured to allow the wearer to have a gas (oxygen) delivered and has filtered exhalation ports for filtering the exhaled gas from the wearer.

The modular pulmonary treatment device 1200 is generally formed of a mask body 1210 that includes a nose portion 1212 for placement over the nose and a mouth portion 1214 for placement over the mouth. The mask body 1210 includes at least one inhalation port 1225 to allow gas to enter the mask to the patient when the inhales and at least one exhalation port 1220 that is configured to allow the patient to exhale.

As shown in FIG. 11, the inhalation port 1225 is configured to receive a gas for delivery inside the mask body 1210 to the patient. The inhalation port 1225 can be an open connector or alternatively, the port 1225 can be provided with and can be in communication with at least one inhalation valve to allow inflow of breathing gas to the patient. As described below, the inhalation port 1225 is fluidly connected to a gas source (not shown) such as by a tube or the like. As described below, any number of other accessories can be attached to the inhalation port 1225 to control the inflow of gas such as a venturi device, nebulizer, a single or dual reservoirs, etc. Many of these accessories allow the level of oxygen to be metered.

It will be appreciated that in one embodiment there is no inhalation valve but instead, the inhalation port 1225 is a port that allows for an accessory to be attached to deliver oxygen. For example tubing or other accessories can be sealingly attached to the port 1225. In other embodiments, an inhalation valve can be provided.

Alternatively, an inhalation filter cartridge can be attached to the inhalation port 1225. The cartridge can include a cartridge body that holds a filter such as the type described herein. The air entering the mask body 1210 is thus filtered as the wearer inhales. This operating mode can be used when the wearer is outdoors entering a store, in high density spaces, etc. The inhalation cartridge is easily detached from the port 1225 allowing the system to convert into a system in which oxygen is delivered via tubing to the port 1225.

The modular pulmonary treatment device 1200 can thus be any number of mask based devices that allow for the controlled delivery of a gas (oxygen) to the patient and of course, allowing the patient to freely exhale.

Any number of techniques can be used to attach the modular pulmonary device 1200 to the main body 1100. For example, an adhesive can be applied along the peripheral edge of the modular pulmonary device 1200 for securing the eye covering 1300 to the main body 1100. Alternatively, the modular pulmonary device 1200 can be stitched to the main body 1100. Any number of other techniques can be used to sealingly attach the modular pulmonary device 1200 to the main body 1100.

More details concerning suitable mask bodies 1210 are disclosed in commonly assigned US patent application publication No. 2016/0158477 and U.S. Pat. No. 9,498,592, each of which is hereby expressly incorporated by reference in its entirety. These documents describe and illustrate a great number of face masks that can comprise the device 1200 and also describe operating modes and accessories that can be used with the modular pulmonary treatment device 1200. For example, a venturi device can be attached to the inlet port 1225 to allow for controlled delivery of oxygen at a selected concentration, such as between 21% and 100% of the total gas delivered to the patient. Thus, a high flow delivery venturi can be used. A nebulizer and/or reservoir collection bag can be used as disclosed in Applicant's own prior work, such as the incorporated by reference documents mentioned herein.

Exhalation Port with Particulate Filter

At least one exhalation port 1220 can include an exhalation filter assembly that can consist of a detachable filter body that holds filter 1250. Alternatively, the exhalation port 1220 can include an exhalation valve assembly that includes the filter 1250 for filtering the exhaled gas. The filter 1250 is positioned such that the exhaled air must pass through the filter 1250 before existing the mask body 1210 into the atmosphere. The filter 1250 is thus preferably configured to filter out virus particles and other pathogens, etc. For example, the filter 1250 can be an N95, N99 or N100 filter.

As described in the '477 publication, in a different embodiment, an exhalation valve and filter 1250 can be part of a detachable cartridge that is detachable from the mask body 1210 to allow for replacement of the filter 1250. In one embodiment, the exhalation valve assembly has a valve seat to which the exhalation valve seats and then the filter 1250 is upstream of the valve so that exhaled air passes through the filter and then passed the open valve. Alternatively, the filter 1250 can be located downstream of the valve so that exhaled air passing by the open valve then contacts and passes through the filter 1250.

When there is no exhalation valve, only the filter 1250 is provided in the cartridge body that is detachably attached to the port 1220 to filter the exhaled air.

In the illustrated mask body 1210, there are two exhalation ports 1220; however, there can only be a single larger port or more than two ports.

It will be appreciated that the protective headgear 1000 is a closed system in that the caregivers are protected from the wearer, while the headgear is configured to allow for flow of oxygen or other gas or a mixture to the patient to treat a respiratory condition.

Figure 12:
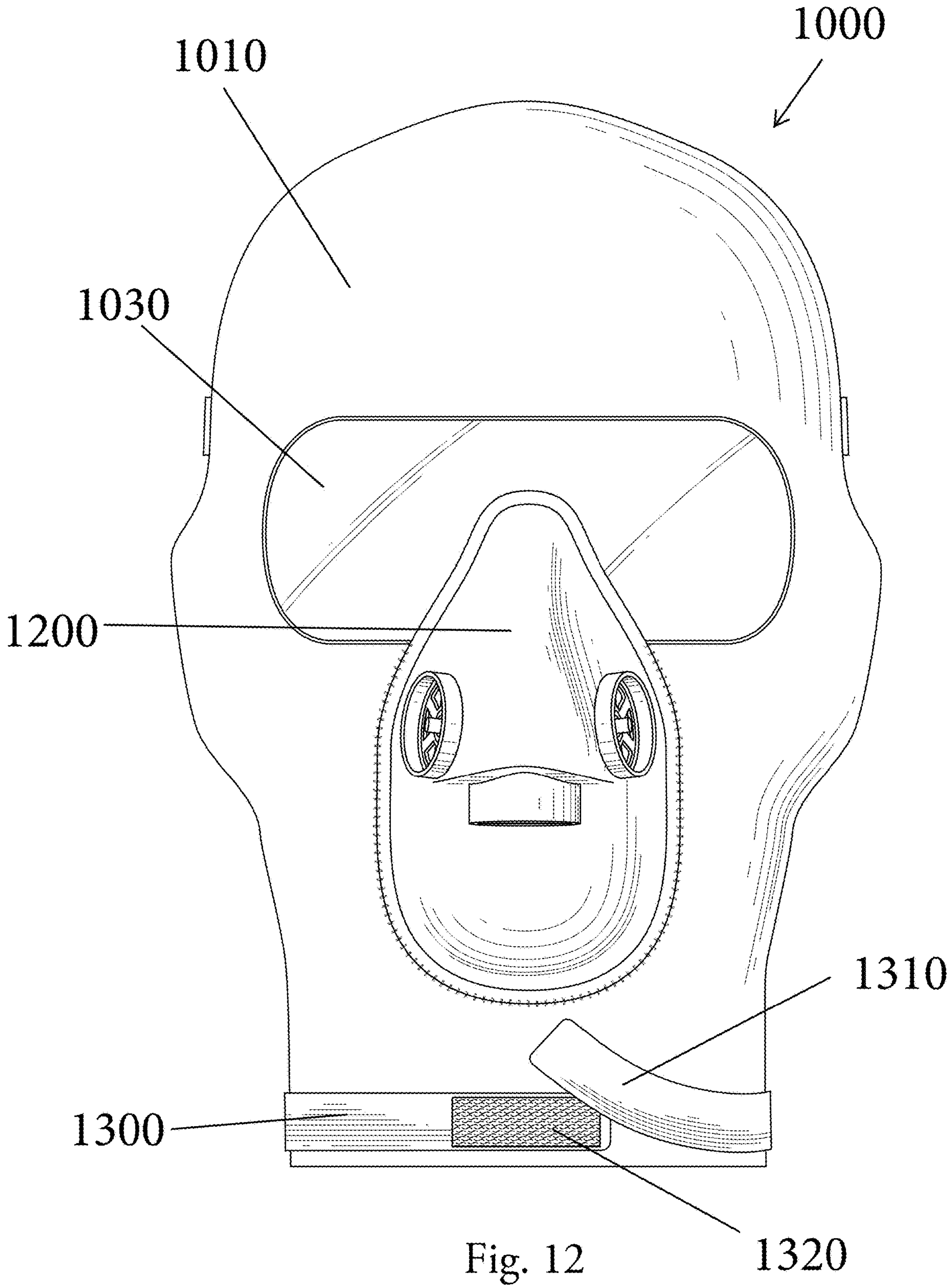
FIG. 12 is a front elevation view of another patient interface.
Figure 13:
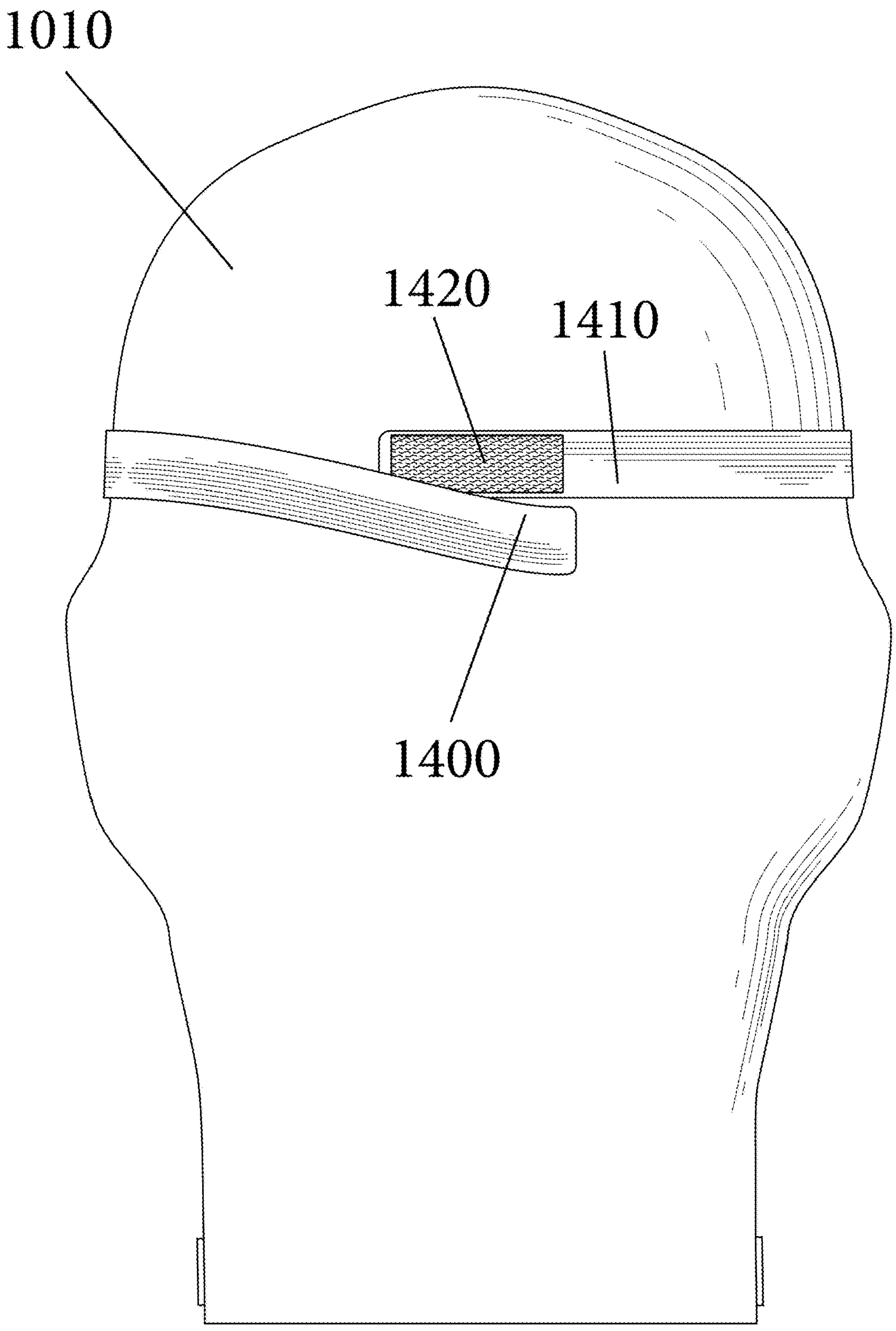
FIG. 13 is a rear elevation view thereof.

Optionally and depending upon the material used to make the main body 1100, one or more tightening elements may be provided for ensuring that the main body 1100 fits tight to the wearer's head. FIG. 12 shows a first strap 1300 that is attached at one end to the body 1100 and a second strap 1310 that is attached at one end to the body 1100. The free end of one or more of the straps 1300, 1310 can include hook and loop fastener 1320 or other fastener to allow the neck portion of the main body 1100 to be tightened. FIG. 13 shows a similar arrangement for the upper head portion of the main body 1100 and includes a first strap 1400 that is attached at one end to the body 1100 and a second strap 1410 that is attached at one end to the body 1100. The free end of one or more of the straps 1400, 1410 can include hook and loop fastener 1420 or other fastener to allow the neck portion of the main body 1100 to be tightened.

Unlike the dead space generated by a combined eye/face shield and a mask, the present invention (headgear 1000) has negligible dead space since the eye covering 1300 is integrated and the only dead space is located in the mask body 1210. However, the interior of the mask body 1210 has a flow of incoming air/delivered oxygen and thus, is truly not a dead space like the one encountered with a front eye/face shield over a mask. Such stream of incoming high pressure gas prevents CO2 buildup, etc.

To allow for patient fluids, such as water or the like, to be delivered, a small orifice can be added to the mask body 1210 that is openable and closeable and by a cover or cap, etc. This is positioned to allow a straw or the like to be inserted to permit drink to enter patient's mouth. Alternatively, a boot for an MDI can be incorporated into the face mask body 1210.

The port 1225 or another inhalation port can be provided in body 1210 for attachment to an MDI to allow for delivery of an aerosol into the mask body 1210 for inhalation by the patient. An MDI spacer can be attached to the face mask body 1210 to allow for attachment to an MDI. Any ports not being used in the mask body 1210 can be closed off with a cap or the like that is sealed to the main body 1210.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

What is claimed is:

1. A patient interface comprising:

a main body that is configured to be worn over a patient's face, the main body having an inhalation port that is for fluid coupling to an inhalation gas source and at least one exhalation port; and a Heat and Moisture Exchanger (HME) unit that has an inhalation leg that is in fluid communication with the inhalation port and a top leg that is in fluid communication with the inhalation leg and the at least one exhalation port, the top leg having an open first end and an open second end opposite the open first end, the top leg comprising a tubular structure that includes a cylindrical shaped side wall that has an arcuate shaped open window formed therein between the open first end and the open second end and being open along the cylindrical shaped side wall of the top leg, the HME unit further including at least one HME membrane that is disposed within the top leg and extends in a longitudinal direction within the top leg adjacent the open window such that the at least one HME membrane completely covers the open window, wherein a longitudinal axis of the at least one HME membrane is coaxial with a longitudinal axis of the top leg.

2. The patient interface of claim 1, wherein the inhalation leg is formed at a 90 degree angle relative to the top leg and the open window extends arcuately along a side circumferential surface of the at least one HME membrane.

3. The patient interface of claim 2, wherein the inhalation leg and the top leg have a T-shape with the top leg being open at the opposite first and second ends.

4. The patient interface of claim 1, wherein the top leg is sealingly coupled to an inner surface of the main body such that (the top leg) is sealed relative to the at least one exhalation port.

5. The patient interface of claim 1, wherein the HME unit includes two adjacent abutting HME membranes that completely cover the open window.

6. The patient interface of claim 1, wherein the at least one exhalation port comprises two exhalation ports that are located on opposite sides of the main body and the opposite open first and second ends of the top leg are sealingly coupled to the two exhalation ports.

7. The patient interface of claim 1, wherein the open window faces upward within the main body.

8. The patient interface of claim 1, further including a detachable filter body that holds a filter and is sealingly coupled to the at least one exhalation port.

9. The patient interface of claim 8, wherein the detachable filter body comprises a cartridge that holds the filter.

10. The patient interface of claim 8, wherein the filter comprises one of a N95 filter, a N99 filter and a N100 filter.

11. The patient interface of claim 1, wherein the main body comprises a face mask.

12. A protective headgear comprising:

a main body configured to be worn over a patient's face, the main body having an inhalation port that is for fluid coupling to an inhalation gas source and a pair of exhalation ports; and an HME unit that has an inhalation leg that is in fluid communication with the inhalation port and a cylindrical shaped top leg that is in fluid communication with the inhalation leg and the pair of exhalation ports, the top leg having an open window formed within a curved side wall of the cylindrical shaped top leg, the HME unit further including at least one cylindrical shaped HME membrane that is disposed within the top leg adjacent the open window such that the of the at least one cylindrical shaped HME membrane completely covers the open window and covers an entrance into the inhalation leg from the cylindrical shaped top leg; and wherein the opposite ends of the top leg are in direct fluid communication the pair of exhalation ports; and a pair of detachable filter bodies each of which holds a filter and is sealingly coupled to one exhalation port of the pair of exhalation ports;

wherein the top leg and the inhalation leg are integrally formed as a single part;

wherein a longitudinal axis of the at least one cylindrical shaped HME membrane is coaxial with a longitudinal axis of the top leg.

13. The patient interface of claim 12, wherein the window is bounded along four sides thereof.

14. The patient interface of claim 12, wherein the HME unit has a T-shape.

15. The patient interface of claim 12, wherein both an inhalation flow path and an exhalation flow path (extend) through the at least one cylindrical shaped HME membrane.

16. The patient interface of claim 12, wherein the main body includes a pair of side strap attachment tabs that are provided on either side of the main body, each attachment tab has one or more slits for receiving a strap that is designed to be fitted about a wearer's head, each slit having a round center opening and two linear end sections.

* * * * *